United States Patent [19]
Flatland

[11] 3,947,965
[45] Apr. 6, 1976

[54] PRESSURIZED DENTAL HANDPIECE

[76] Inventor: Lloyd P. Flatland, 15 Quisisana Drive, Kentfield, Calif. 94904

[22] Filed: Aug. 5, 1974

[21] Appl. No.: 494,542

[52] U.S. Cl. .................................................. 32/26
[51] Int. Cl.² .......................................... A61C 1/08
[58] Field of Search .............. 32/22, 26, 27, DIG. 3; 415/503

[56] References Cited
UNITED STATES PATENTS

| | | | |
|---|---|---|---|
| 3,189,999 | 6/1965 | Reiter | 32/27 |
| 3,210,848 | 10/1965 | Bizzigotti | 32/27 |
| 3,364,576 | 1/1968 | Kern, Jr. | 32/27 |
| 3,858,323 | 1/1975 | Flatland | 32/27 |

Primary Examiner—Louis G. Mancene
Assistant Examiner—Jack Q. Lever
Attorney, Agent, or Firm—Lothrop & West

[57] ABSTRACT

A pressurized dental handpiece has a housing in which a shaft is journalled and from which the shaft projects to support a dental tool. A high speed air turbine runner is on the shaft and is propelled by air under superatmospheric pressure brought to a nozzle for the runner through a conduit. A tubular extension of the housing surrounds the conduit and is in communication with the housing to serve as the turbine exhaust duct to the atmosphere. An adjustable valve regulates the spent exhaust air flowing from the extension to maintain a superatmospheric pressure in the extension. Some spent air is allowed to flow from the extension around the discharge of a water tube passing through the extension and the housing in the direction of the projecting shaft and dental tool.

3 Claims, 2 Drawing Figures

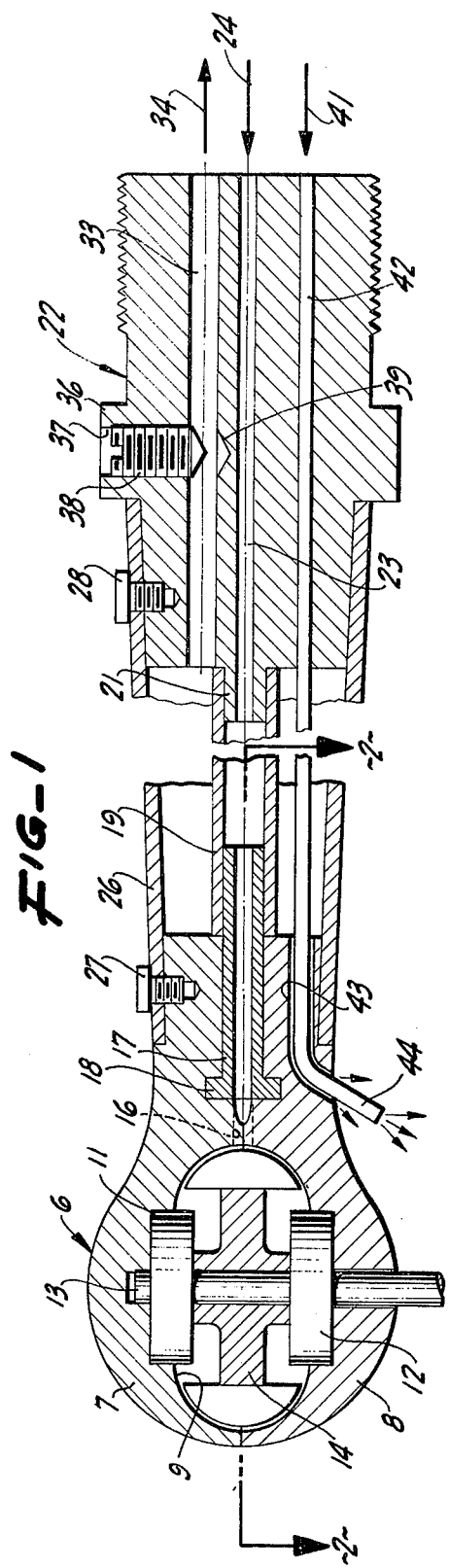
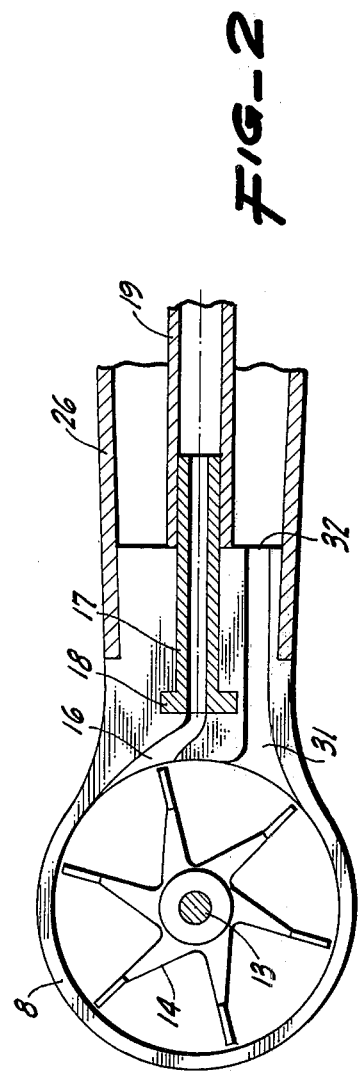

PRESSURIZED DENTAL HANDPIECE

There are presently available high-speed, air-operated turbine dental handpieces, such as shown in my copending application entitled "Dental Handpiece", filed Oct. 27, 1972 with Ser. No. 301,263, now U.S. Pat. No. 3,858,323 issued Jan. 7, 1975 in which the turbine rotor is extremely small in mass and diameter and operates at a speed in excess of 400,000 revolutions a minute. It is highly important to maintain a proper ambience or operating space for the turbine, in order that the desired speed can be properly maintained, not only initially but for a long period of operation. It is also of importance to provide appropriate air passageways for the turbine, so that a sufficient quantity of air can flow to it and equally importantly can flow from it.

An object of the invention is to provide a pressurized dental handpiece in which extraneous materials, both those produced by the dental tool which is propelled and those from other extraneous sources, are generally maintained away from the operating machinery.

Another object of the invention is to provide a dental handpiece in which the operation of the turbine can be, in part, regulated by controlling its exhaust.

Another object of the invention is to provide an appropriate mouth spray in connection with the dental handpiece.

A further object of the invention is to provide a substantially improved dental handpiece, particularly one of the pressurized, air turbine type.

Other objects, together with the foregoing, are attained in the embodiment of the invention described in the accompanying description and illustrated in the accompanying drawings, in which:

FIG. 1 is a cross-section on a longitudinal plane through a pressurized dental handpiece constructed pursuant to the invention, portions being broken away to reduce the extent of the figure; and FIG. 2 is a cross-section of a portion of the structure of FIG. 1, the plane of section being indicated by the line 2—2 of FIG. 1.

In the particular dental handpiece chosen for illustration herein, the mechanical construction is substantially the same as shown in my above-identified application. In that instance the turbine runner is within a housing split into two portions of a diametral plane, the split portions opening into a tubular handpiece. Substantially the same arrangement is employed herein. In this embodiment there is provided a housing 6 made up of two hemispherical members 7 and 8 divided along the plane of the section line 2—2 shown in FIG. 1, and which are contoured to afford an internal turbine chamber 9. The two members of the housing 6 are fastened together in any suitable fashion, not shown, and position between them, when assembled, a pair of high-speed bearings 11 and 12. These are mounted in the housing and support a high-speed, rotary shaft 13 extending out of the housing and intended to be provided with a chuck or other mechanism for supporting and operating a dental tool, such as a bur (not shown).

On the shaft 13 is mounted the runner 14 of a high-speed turbine arranged to receive incoming high pressure, or superatmospheric pressure, air through a nozzle 16. To supply the nozzle, there is afforded an air tube 17 having a flange 18 captured between the housing portions 7 and 8 and extending into a somewhat flexible tube 19, in turn fitted over a hub 21 on a terminal block 22 having a bore 23 continuing communication with the tube. Air under relatively high, superatmospheric pressure is brought into the bore 23 from a suitable source (not shown) as indicated by and in the direction of the arrow 24.

To protect the tubing 19 and the various other parts, and to provide a unitary structure, there is a relatively rigid housing extension 26. This is generally tubular or conical in form and of thin-walled metallic or stiff plastic construction. It is telescoped over one end of the housing 6 and is likewise telescoped over one end of the block 22, being removably fastened in place in each instance by screws 27 and 28. In this way there is afforded a suitable supply of air to operate the turbine.

To afford an appropriate exhaust or spent air discharge, the housing 6 includes an exhaust duct 31 converging into a discharge port 32 opening into the interior of the relatively air-tight extension 26. Air which is released to the interior of the extension is able to flow therefrom through a conduit 33 leading to the atmosphere in the direction of and as indicated by the arrow 34.

Particularly in accordance with the invention it is desired to maintain a certain amount of back pressure or superatmospheric pressure within the interior of the housing 26 and its immediately communicating members. For that reason, the block 22 is provided with an integral ring 36 through one portion of which extends a threaded passageway 37. A screw 38 is rotatable in the passageway by an appropriate tool and serves as a valve. The valve can be positioned anywhere from fully open out of the conduit 33 to a closed position in contact with a seat 39.

By variously positioning the valve the resistance to flow in the passageway 33 can be varied, so that the pressure within the extension 26 can be set at any selected value. The elevated or superatmospheric pressure is effective to supply slight leakage wherever there is an opening to the outside, so that there is little or no opportunity for any exterior material to work its way through such opening into the interior of the structure. Furthermore, the operation of the turbine can be somewhat regulated by varying its exhaust pressure.

More particularly, the spent or exhaust air under the superatmospheric pressure within the extension is utilized to assist in the dental operation. For that reason, a duct 42 extends through the member 22 from a source of water (not shown) as represented by and flowing in the direction of the arrow 41. The duct 42 not only goes through the member 22 but passes entirely through the extension 26 and travels through a substantially larger passageway 43 in the housing 6. The duct 42 or pipe has an angled discharge portion 44 directed generally toward the shaft 13 in its extended portion, or toward a dental tool which is mounted thereon. The enlarged passage 43 follows a similar path and is slightly spaced from the tube 44.

Air under pressure within the extension follows along the tube 42 on the outside thereof, and discharges around the outside of the water jet discharging from the end 44 of the tube. A spray or stream of water and air is projected toward the rotating shaft 13 and any tool thereon. Because there may also be a slight leakage of interior pressure air through the bearing 12 and along the wall of the half housing 8 next to the extended portion of the shaft 13, there is no opportunity for extraneous material to work in at these locations which are most subject to the dental debris incident upon use of the device.

What is claimed is:

1. A pressurized dental handpiece comprising a housing, a shaft journalled in and projecting from said housing, a rotor within said housing and fast on said shaft, a generally closed tubular extension from said housing and interiorly communicating therewith, a conduit for high pressure air passing through said extension and communicating with the interior of said housing adjacent said rotor, means opening the interior of said extension to the atmosphere, and means including a valve for restricting air flow in said opening means.

2. A device as in claim 1 in which said means for restricting is an adjustable valve.

3. A device as in claim 1 including a water tube extending through said extension and ending at a location near the projection of said shaft from said housing, and including means forming an air passage around said water tube and extending from the interior of said extension to the atmosphere substantially at said location.

* * * * *